(12) United States Patent
Nguyen et al.

(10) Patent No.: US 11,603,435 B2
(45) Date of Patent: Mar. 14, 2023

(54) HYDROPHILIC POLYSILOXANE ELASTOMER

(71) Applicant: Dow Silicones Corporation, Midland, MI (US)

(72) Inventors: Kimmai T. Nguyen, Midland, MI (US); Kenneth E. Zimmerman, Midland, MI (US); Donald Kadlec, Midland, MI (US); Hannah Wedge, Midland, MI (US); Nisaraporn Suthiwangcharoen, Midland, MI (US)

(73) Assignee: DOW SILICONES CORPORATION, Midland, MI (US)

( * ) Notice: Subject to any disclaimer, the term of this patent is extended or adjusted under 35 U.S.C. 154(b) by 364 days.

(21) Appl. No.: 16/787,086

(22) Filed: Feb. 11, 2020

(65) Prior Publication Data
US 2020/0262980 A1 Aug. 20, 2020

Related U.S. Application Data

(60) Provisional application No. 62/806,997, filed on Feb. 18, 2019.

(51) Int. Cl.
| C08G 77/44 | (2006.01) |
| A61K 8/91 | (2006.01) |
| A61Q 19/00 | (2006.01) |
| C08G 77/00 | (2006.01) |

(52) U.S. Cl.
CPC .............. C08G 77/44 (2013.01); A61K 8/91 (2013.01); A61Q 19/00 (2013.01); A61K 2800/48 (2013.01); C08G 77/70 (2013.01)

(58) Field of Classification Search
CPC .......... C08L 83/00; C08L 83/04; C08L 83/12; C08L 83/08; C08L 51/06; C08L 83/06; C08L 71/02; C08L 83/10; C08L 23/26; C08L 83/14; C08L 2205/025; C08L 2205/03; C08L 2312/08; C08L 2205/035; C08L 2205/02; C08L 75/04; C08L 2203/20; C08L 2201/52; C08L 2666/02; C08L 33/08; C08L 43/04; C08L 101/10; C08L 2201/00; C08L 2201/10; C08L 2203/162; C08L 2203/206; C08L 23/0815; C08L 2312/00; C08L 51/085; C08L 53/00; C08L 53/005; C08L 63/00; C08L 71/08; C08L 1/08; C08L 2201/02; C08L 2201/08; C08L 2203/16; C08L 2203/18; C08L 2203/202; C08L 2203/30; C08L 23/00; C08L 23/06; C08L 23/08; C08L 2310/00; C08L 2312/06; C08L 27/06; C08L 31/04; C08L 33/02; C08L 33/06; C08L 51/003; C08L 63/10; C08L 69/00; C08L 71/00; C08L 75/06; C08L 97/02; A61Q 19/00; A61Q 5/02; A61Q 5/12; A61Q 5/00; A61Q 15/00; A61Q 17/04; A61Q 19/08; A61Q 1/02; A61Q 11/00; A61Q 19/10; A61Q 1/10; C08G 77/12; C08G 77/20; C08G 77/18; C08G 18/10; C08G 77/14; C08G 77/46; C08G 77/70; C08G 77/26; C08G 77/50; C08G 77/44; C08G 18/3203; C08G 18/61; C08G 18/6715; C08G 18/755; C08G 18/242; C08G 18/244; C08G 18/289; C08G 18/4829; C08G 18/5096; C08G 18/7671; C08G 2190/00; C08G 65/336; C08G 65/34; C08G 77/16; C08G 77/388; C08G 77/48; C08G 18/18; C08G 18/4283; C08G 18/44; C08G 18/4825; C08G 18/4841; C08G 18/4845; C08G 18/73; C08G 18/8166; C08G 77/38; C08G 77/392; A61K 8/895;
(Continued)

(56) References Cited

U.S. PATENT DOCUMENTS

| 5,236,986 A | 8/1993 | Sakuta |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,891,977 A | 4/1999 | Dietz et al. |
| | (Continued) | |
| 5,880,210 A | 3/1999 | Schulz, Jr. et al. |

FOREIGN PATENT DOCUMENTS

| EP | 2014701 B1 | 11/2010 |
| EP | 2167014 B1 | 10/2011 |
| | (Continued) | |

*Primary Examiner* — Audrea B Coniglio
*Assistant Examiner* — Audrea Buckley
(74) *Attorney, Agent, or Firm* — Steven Mork

(57) ABSTRACT

An elastomer has the general structure of:

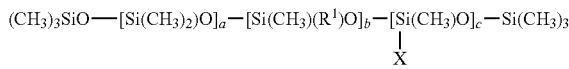

where: subscript a is 50-500, b is 1-10, c is 2-30, $R^1$ has the structure:

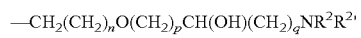

where n, p and q are each independently 1-5 and $R^2$ and $R^{2'}$ are independently selected from alkyl and hydroxyalkyl groups having 1-5 carbon atoms; where X is a crosslinker remnant bound to a siloxane unit corresponding to subscript c of a siloxane backbone polymer in addition to the one shown so that the crosslinker remnant in each occurrence is a reaction product with two siloxane backbone polymers, wherein the crosslinker is selected from a group consisting of primary organic dienes, divinyl siloxane and polyoxyalkylenes wherein at least two X components correspond to crosslinker remnants connecting the same two siloxane backbone polymers.

10 Claims, No Drawings

(58) Field of Classification Search
CPC ............... A61K 8/062; A61K 2800/10; A61K 2800/54; A61K 8/891; A61K 8/898; A61K 2800/48; A61K 8/892; A61K 8/894; A61K 2800/21; A61K 2800/31; A61K 2800/5426; A61K 2800/592; A61K 8/04; A61K 8/06; A61K 8/19; A61K 8/25; A61K 8/29; A61K 8/585; A61K 8/8194; A61K 8/86; A61K 2800/262; A61K 2800/412; A61K 2800/612; A61K 2800/654; A61K 8/068; A61K 8/893; A61K 8/899; A61K 8/90; A61K 8/91; A61K 8/92; A61K 9/70; A61K 9/7069

See application file for complete search history.

(56) References Cited

U.S. PATENT DOCUMENTS

| | | | |
|---|---|---|---|
| 6,200,581 B1 | 3/2001 | Lin et al. | |
| 6,262,170 B1 | 7/2001 | Kilgour et al. | |
| 6,331,604 B1 | 12/2001 | Wang et al. | |
| 6,365,670 B1 | 4/2002 | Fry | |
| 6,503,519 B1 | 1/2003 | Sakuta | |
| 7,781,505 B2 * | 8/2010 | Cook | C08K 5/5419 |
| | | | 524/261 |
| 8,586,669 B2 | 11/2013 | Kennan et al. | |
| 9,585,832 B2 | 3/2017 | Tamura et al. | |

FOREIGN PATENT DOCUMENTS

| | | |
|---|---|---|
| WO | 2014121037 A8 | 8/2014 |
| WO | 2017196524 | 11/2017 |

\* cited by examiner

HYDROPHILIC POLYSILOXANE ELASTOMER

BACKGROUND OF THE INVENTION

Field of the Invention

The present invention relates to a siloxane elastomer and a formulation comprising the siloxane elastomer.

Introduction

Siloxane elastomers are useful in cosmetic formulations to enhance the viscosity and feel of the final product. A challenge with such siloxane elastomers is that they need to be compatible with various organic solvents commonly used in cosmetics while at the same time be sufficiently hydrophilic to have a high water uptake.

To achieve the desired performance properties, siloxane elastomers often contain polyalkoxy groups, particularly pendant polyalkoxy groups. There is an increasing movement in the cosmetic industry, however, to reduce polyalkoxy functionality in cosmetics. It is particularly desirable to minimize the extent of pendant polyalkoxy functionality because pendant functionalities are more exposed and labile than polyalkoxy groups internally bound within a polymer.

It is desirable to identify a new siloxane elastomer that is sufficiently hydrophilic so as to achieve 50 weight-percent water uptake or more and is compatible with key organic solvents used in the cosmetic industry. More desirable is such a siloxane elastomer that also is free of pendant polyalkoxy groups. Yet more preferably is such a siloxane elastomer that is free of polyalkoxy groups.

BRIEF SUMMARY OF THE INVENTION

The present invention solves the problem of identifying a new siloxane elastomer that achieves 50 weight-percent water uptake or more and is compatible with key organic solvents used in the cosmetic industry. The present invention also provides such a siloxane elastomer that is free of pendant polyalkoxy groups. The present invention further provides such a siloxane elastomer that is free or polyalkoxy groups.

The present invention is a result of surprisingly discovering certain aminofunctional pendant groups when present on crosslinked polysiloxanes provide the desired properties identified for siloxane elastomers for use in cosmetic formulations, even in an absence of poly(alkylene oxide) pendant groups and even in an absence of poly(alkylene oxide) group of any kind.

In a first aspect, the invention is an elastomer comprising multiple siloxane backbone polymers interconnected by two or more than two crosslinker remnants where the elastomer has the general structure of Formula (I):

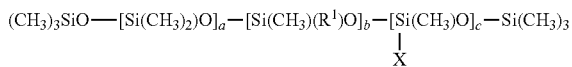

(I)

where:
subscript a is independently in each siloxane backbone polymer a number in a range of 50 to 500,
subscript b is independently in each siloxane backbone polymer a number in a range of one to 10,
subscript c is independently in each siloxane backbone polymer a number in a range of 2 to 30, and $R^1$ has the structure of Formula (II):

(II)

where subscripts n, p and q are each independently in each occurrence a number in a arrange of one to 5 and $R^2$ and $R^{2'}$ are independently in each occurrence selected from a group consisting of alkyl and hydroxyalkyl groups having one or more and at the same time 5 or fewer carbon atoms; and where X is a crosslinker remnant bound to a siloxane unit corresponding to subscript c of a siloxane backbone polymer in addition to the one shown so that the crosslinker remnant in each occurrence is a reaction product with two siloxane backbone polymers, wherein the crosslinker is selected from a group consisting of primary organic dienes, divinyl siloxane and polyoxyalkylenes wherein at least two X components correspond to crosslinker remnants connecting the same two siloxane backbone polymers.

In a second aspect, the invention is a formulation comprising the elastomer of the first aspect in combination with an organic solvent. The elastomer of the present invention is useful for making cosmetic formulations of the present invention. The cosmetic formulations of the present invention are useful for a variety of cosmetic applications.

DETAILED DESCRIPTION OF THE INVENTION

Test methods refer to the most recent test method as of the priority date of this document when a date is not indicated with the test method number. References to test methods contain both a reference to the testing society and the test method number. The following test method abbreviations and identifiers apply herein: ASTM refers to ASTM International; EN refers to European Norm; DIN refers to Deutsches Institut fur Normung; and ISO refers to International Organization for Standards.

"Multiple" means two or more. "And/or" means "and, or as an alternative". All ranges include endpoints unless otherwise indicated. Products identified by their tradename refer to the compositions available from the suppliers under those tradenames at the priority date of this document unless otherwise stated herein.

The elastomer of the present invention comprise multiple siloxane backbone polymers interconnected by two or more than two crosslinker remnants. Elastomers are crosslinked polymers. In the present invention, the crosslinked polymers are siloxane polymers—the siloxane backbone polymers. The siloxane backbone polymers are crosslinked by "crosslinker remnants", which are crosslinkers as they exist after reacting to crosslink two of the siloxane backbone polymers.

The elastomer of the present invention generally has the structure of Formula (I):

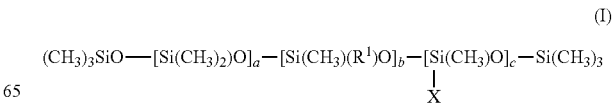

(I)

where:

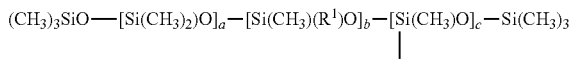

corresponds to a "siloxane backbone polymer". Each siloxane backbone polymer of the elastomer has such a structure. Subscripts a, b and c correspond to an average number of specific siloxane units in a particular siloxane backbone polymer. For instance, $Si(CH_3)_2O$— is the siloxane unit corresponding to subscript a. Although Formula (I) illustrates the siloxane backbone polymer in "block" form such a designation is for clarity and is not limiting. The siloxane backbone backbone can be a random copolymer with siloxane units corresponding to subscripts a, b and c in any order or distributions in the siloxane backbone polymer provided the total number of siloxane units corresponding to each subscript in a particular siloxane backbone polymer adds up to the limitations for the subscript set forth below. The siloxane backbone polymer can have all of the siloxane units corresponding to a particular subscript in a single block for any of the particular siloxane units or any combination of siloxane units.

Subscript a is independently in each siloxane backbone polymer 50 or more, and can be 75 or more, 85 or more, 95 or more, or 100 or more while at the same time is typically 500 or less, and can be 400 or less, 300 or less, and even 200 or less. Generally, subscript a is a number in a range of 50 to 500, preferably 50 to 200.

Subscript b is independently in each siloxane backbone polymer one or more, and can be 2 or more, 3 or more 4 or more 5 or more 6 or morel or more 8 or more and even 9 or more while at the same time is typically 10 or less and can be 9 or less, 8 or less, 7 or less, 6 or less, 5 or less, 4 or less 3 or less and even 2 or less. Generally, subscript b is a number in a range of one to 10.

Subscript c is independently in each siloxane backbone polymer 2 or more, and can be 3 or more, 4 or more, 5 or more, 6 or more 7 or more 8 or more, 9 or more, even 10 or more, while at the same time is generally 30 or less, and can be 25 or less, 20 or less, 15 or less, 10 or less, 9 or less 8 or less, 7 or less, 6 or less, 5 or less, 4 or less or even 3 or less. Typically, subscript c is a number in a range of 2 to 30, preferably a number in a range of 2 to 15 and more preferably in a range of 2 to 8.

The values for each of subscripts a, b, and c can be the same or different in different siloxane polymer backbone of the elastomer, but are typically the same (plus or minus one) in each siloxane polymer backbone. That is, each value of subscript a is typically within one of any other value of subscript a in a particular elastomer and likewise for each value of subscripts b and c.

$R^1$ has the structure of Formula (II):

$$—CH_2(CH_2)_nO(CH_2)_pCH(OH)(CH_2)_qNR^2R^{2'}\quad (II)$$

where:

Subscripts n, p and q correspond to an average number of the specified alkylene units in $R^1$ at that particular location in $R^1$. Subscript n is independently in each occurrence one or more and can be 2 or more, 3 or more and even 4 or more while at the same time is generally 5 or less and can be 4 or less, 3 or less or even 2 or less. Subscript p is independently in each occurrence one or more and can be 2 or more, 3 or more and even 4 or more while at the same time is generally 5 or less and can be 4 or less, 3 or less or even 2 or less.

Subscript q is independently in each occurrence one or more and can be 2 or more, 3 or more and even 4 or more while at the same time is generally 5 or less and can be 4 or less, 3 or less or even 2 or less. The values for subscripts n, p and q can be the same or different from one another but are typically the same for each $R^1$ in the elastomer (that is, each subscript n can be the same for all $R^1$ groups in the elastomer, and so on for subscripts p and q).

$R^2$ and $R^{2'}$ are independently in each occurrence selected from a group consisting of alkyl and hydroxyalkyl groups having one or more and at the same time 5 or fewer carbon atoms. Each $R^2$ can be the same in each occurrence of $R^1$. At the same time, each $R^{2'}$ can be the same or different in each occurrence of $R^1$. At the same time, $R^2$ and $R^{2'}$ can be the same or different in each occurrence of $R^1$. Preferably, $R^2$ and $R^{2'}$ are independently selected from hydroxyalkyl groups and more preferably from a group consisting of $—CH_2CH_2OH$, $—CH_2CH(OH)CH_3$, and $—CH_2CH_2CH_2OH$.

Desirably, $R^1$ has the structure of Formula (III):

$$—CH_2(CH_2)_2OCH(OH)CH_2N[CH_2CH(OH)CH_3]_2 \quad (III)$$

In Formula (I), X is a crosslinker remnant bound to a siloxane unit corresponding to subscript c in another siloxane backbone polymer in addition to the siloxane backbone polymer shown in Formula (I). X represents both the crosslinker remnant and the other siloxane backbone polymer it is connecting to the illustrated siloxane backbone polymer. At least two X groups Formula (I) correspond to crosslinker remnants connecting the same to siloxane polymer backbones, thereby creating crosslinked siloxane polymer backbones. Hence, Formula (I) indicates a crosslinked elastomer comprising multiple siloxane backbone polymers interconnected by multiple crosslinker remnants.

Each crosslinker remnant corresponds to the reaction product of a crosslinker with two siloxane backbone polymers. Desirably, the crosslinker that forms to create the crosslinker remnant is selected from a group consisting of primary organic dienes, divinyl siloxanes and polyoxyalkylenes. Preferably, the crosslinker is selected from a group consisting of primary organic dienes and divinyl siloxanes. The primary organic dienes have carbon double bonds at each end of the molecule, each in a primary position. The organic diene can be an alkene with carbon-carbon double bonds in the primary position at each end of the alkene. Examples of suitable primary organic dienes include any selected from a group consisting of 1,3-butadiene, 1, 4-pentadiene, 1,5-hexadiene, 1,6-heptadiene, 1,7-octadiene. Examples of suitable divinyl siloxanes include any one or combination of more than one selected from a group consisting of dimethylvinylsiloxy terminated polydimethylsiloxane. Examples of suitable polyoxyalkylenes include $CH_2=CHCH_2[OCH(CH_3)CH_2]_{20}CH_2CH=CH_2$ (available as DUS-80 from Nippon Oil and Fats) and as well $CH_2=C(CH_3)CH_2[OCH_2CH_2]_{13}CH_2C(CH_3)=CH_2$ (available as DMUS-5 from Nippon Oil and Fats).

Suitable crosslinker remnants can be selected from alkylenes, linear polysiloxanes, branched polysiloxanes, and polyalkyloxides. Examples of suitable crosslinker residuals include those having the structures of Formulae (IV)-(VII):

$$—CH_2(CH_2)_gCH_2— \quad (IV)$$

$$—CH_2CH_2CH_2[OCH(CH_3)CH_2]_hCH_2CH_2CH_2— \quad (V)$$

$$—CH_2CH(CH_3)CH_2[OCH_2CH_2]_jCH_2CH(CH_3)CH_2— \quad (VI)$$

$$—CH_2CH_2Si(CH_3)_2[OSi(CH_3)_2]_kOSi(CH_3)_2CH_2CH_2— \quad (VII)$$

where:

Subscript g has a value of 2 or more, 3 or more, 4 or more, 5 or more, 6 or more, 7 or more, even 8 or more and at the same time generally has a value of 30 or less, 25 or less, 20 or less, 15 or less, 10 or less, and can be 8 or less, 7 or less, 6 or less, 5 or less, 4 or less or even 3 or less. Formula (IV) represents the crosslinker residual of primary terminal alkenes. For example, when g is 2, Formula (IV) represents the crosslinker of 1,3-butadiene.

Subscript h is desirably one or more, preferably 2 or more, 3 or more, 4 or more 5, or more, 10 or more, 15 or more, 20 or more, 30 or more, 40 or more 50 or more 60 or more and even 70 or more while at the same time is generally 130 or less, 127 or less, 125 or less, 120 or less, 110 or less 100 or less, 75 or less, 50 or less, 40 or less, 30 or less or 20 or less.

Subscript j is desirably one or more, preferably 2 or more, 3 or more, 4 or more, 5 or more, 6 or more, 7 or more 8 or more, 9 or more, 10 or more, 11 or more, 12 or more, 13 or more and can be 14 or more, 15 or more, 20 or more, 25 or more, even 30 or more while at the same time is generally 40 or less, 35 or less, 30 or less, 25 or less, 20 or less, even 15 or less.

Subscript k is desirably 6 or more, preferably 10 or more, 15 or more, 20 or more, 25 or more, 30 or more, 35 or more, 40 or more, 45 or more, 46 or more, and can be 48 or more, 50 or more, 75 or more, 80 or more even 100 or more, 150 or more, 200 or more, 250 or more, 300 or more, even 350 or more while at the same time is generally 500 or less, 450 or less, 400 or less, 350 or less, 300 or less, 250 or less, 200 or less, 150 or less, 100 or less or even 50 or less.

Formula (I) is the "general structure" for the elastomer of the present invention. That means Formula (I) represents the major composition of the elastomer, but slight deviations from Formula (I) are still assumed within the scope of Formula (I). Slight deviations are variants of Formula (I) that in correspond to 5 mole-percent or less, preferably 4 mole-percent or less, more preferably 3 mole-percent or less, even more preferably 2 mole-percent or less and most preferably one mole-percent or less relative to moles of siloxane backbone polymer in the elastomer are still considered within the scope of Formula (I). For example, the elastomer may contain a minor amount of crosslinker bound to only one siloxane backbone polymer, thereby forming a pendant crosslinker group extending off from a siloxane backbone polymer. Such a variant from the express structure of Formula (I) would still be considered within scope of Formula (I) provided the total number of such pendant crosslinker groups is within the scope of variants stated above.

There is an increasing desire in the cosmetic industry to reduce poly(alkylene oxide) components in cosmetic components. Pendant poly(alkylene oxide) groups are less desirable than poly(alkylene oxide) crosslinkers. "Pendant" groups extend off from a siloxane backbone polymer and are only bound to one siloxane backbone polymer in one location. Pendant alkoxy groups are more exposed, more mobile and generally more labile than poly(alkylene oxide) crosslinkers. Desirably, the elastomer of the present invention contains less than one mole-percent, preferably less than 0.5 mole-percent and more desirably is free of pendant poly(alkylene oxide) groups, where mole-percent pendant poly(alkylene oxide) groups are relative to moles of siloxane backbone polymers as determined by nuclear magnetic resonance spectroscopy (proton NMR and/or a combination of $^{29}$Si and $^{13}$C NMR). It is even more desirable for the elastomer to be free of alkoxy crosslinker residuals.

It is suitable to prepare the elastomers of the present invention by synthesis methods known in the art. Typically, the elastomers are prepared by crosslinking a siloxane backbone polymer by hydrosilylation. Hydrosilylation reactions are well known in the art for addition reactions of Si-H bonds across unsaturated bonds. The siloxane backbone polymer contains SiH bond at the siloxane unit where crosslinking will occur. Additionally the siloxane backbone polymer contains the specified pendant $R^1$ group. Addition of the pendant $R^1$ group to a siloxane backbone polymers can be done by known reactions, such as amination reactions, at any time but preferably prior to crosslinking. Typically, the hydrosilylation reaction to prepare the elastomer is run in an organic solvent. The organic solvent can be stripped away from the elastomer prior to using the elastomer yielding neat elastomer, or the organic solvent can remain with the elastomer as a formulation comprising the elastomer and the organic solvent.

The structure of the siloxane backbone polymer and elastomers are best determined from the structure of the starting materials and the stoichiometric ratios of the starting materials used to make the elastomers. Given an elastomer, characterization by Fourier transform infrared spectroscopy (FTIR), digestive gas chromatography and nuclear magnetic resonance spectroscopy ($^1$H, $^{13}$C, and $^{29}$Si) should provide sufficient information to discern the elastomer structure, including values for subscripts a, b, c, h, j, k, n, p, and q used in Formulas herein as well as identification of pendant groups and mole-percents of pendant groups and alkoxy groups.

The elastomer can be neat or can be formulated with an organic solvent, such as a solvent in which the elastomer was prepared. One of the desirable features of the elastomer of the present invention is that it is both compatible with organic solvents, particularly those suitable for use in cosmetic and personal care applications, as well as water.

Organic Solvent Compatibility

Compatibility with organic solvents is evident by evaluating clarity and viscosity of a formulation prepared by adding 3.75 g of silicone elastomer blend to 11.25 g of a specified solvent (C12/15 alkyl benzoate for Table 2, caprilyic/carpic triglyceride for Table 3 and ethanol for Table 4) in a 20 g dental cup and mixing the combination in a Speed Mixer™ DAC 150V from Flacktek for 30 seconds at 3500 revolutions per minute. Transfer the mixed material to a glass vial for visual evaluation. If the formulation visually appears homogeneous and ranks clear (10), or only slightly hazy (8) and with a viscosity rank of 10—viscous enough that it does not pour when inverted—then the elastomer if deemed "compatible" with the organic solvent. For haziness, rank the samples by visual inspection as clear (10), slightly hazy (8), hazy (5), cloudy (3), opaque (1), incompatible—phase separate (0). Rank the viscosity as does not pour when inverted (10), barely pourable when inverted similar to 300M cst PDMS (9), pourable similar to 60M cst PDMS (5), pourable similar to 10M cst PDMS (3) or liquid similar to 245 fluid (1).

Water Compatibility (Water Uptake Screening)

To have desirable compatibility with aqueous solutions, the elastomer must demonstrate at least 50 weight-percent water uptake in the following screening method. Conduct the screening using a Speed Mixer™ DAC 150V from FlackTek. Into their 20 gram (g) Max cup add 2.0 g of the elastomer blend (for instance, those of Example 1, 2, 3 or 4). Shear the elastomer at 3500 revolutions per minute for thirty seconds. Add 1.0 g of water to the 20 g Max cup containing the sheared elastomer. Shear the combination of water and elastomer for 30 seconds at 3500 revolutions per minute. If the elastomer absorbs the water after shearing, repeat by adding another 1.0 g portion of water and shear for another 30 seconds at 3500 revolutions per minute. Continue until the elastomer no longer absorbs the added water after shearing (that is, beads of water are evident with the elastomer). Calculate total water uptake as a weight percentage of water in the elastomer when it no longer absorbs water:

% water uptake=100×[(grams of water absorbed)/(grams water absorbed+grams of elastomer)]

One desirable application for the elastomers of the present invention is in formulation cosmetic and personal care products. In such applications, the elastomer or the elastomer in combination with an organic solvent may be formulated with a continuous aqueous phase. The aqueous phase can be water or a water-continuous solution. Alternatively, the elastomer can be formulated into an organic continuous phase such as a wax or oil. In addition to the aqueous continuous phase, the elastomer (or combination of elastomer and organic solvent) can be formulated with further components desirable for cosmetic and/or personal care products including any one or any combination of more than one component selected from a group consisting of anionic surfactants, cationic polymers, fatty acid alkanolamides, amine oxides, acyl derivatives, polyols, oils, waxes, vitamins, colorants, and fragrant additives.

Hence, the present invention includes formulations of the elastomer with an organic solvent and/or an aqueous or organic continuous phase. The formulations of the present invention can further comprise components desirable for cosmetic and/or personal care products including any one or any combination of more than one component selected from a group consisting of anionic surfactants, cationic polymers, fatty acid alkanolamides, amine oxides, acyl derivatives, polyols, oils, waxes, vitamins, colorants, and fragrant additives. Formulations of the present invention can be personal care products which are useful to maintain personal hygiene and/or physical appearance. Particularly desirable formulations of the present invention are cosmetics that enhance physical appearance. Formulations can be in the form of creams (for example, moisturizers, hand sanitizer, shaving cream, shower gel, and/or make-up), sticks (for example, lipstick, lip gloss, soap, deodorant, and/or antiperspirant), and fluids (for example, shampoo, liquid soap, and hand sanitizer).

EXAMPLES

Synthesis of $R^1$ Precursor

Provide a 3-neck round bottom flask equipped with a reflux condenser, nitrogen sweep, stirrer, temperature controller with thermocouple and a heating mantle. Add to the flask 79.17 grams (g) bis(2-hydroxypropyl)amine (DIPA) that is preheated to 50 degrees Celsius (° C.) and 37.29 g isopropanol. Heat the contents to 50° C. Add dropwise 70 g allyl glycidyl ether and allow the reactants to undergo amination for approximately 15 hours at 70° C. while stirring. Reconfigure the flask for simple distillation. Remove the isopropanol and excess allyl glycidyl ether by vacuum stripping at 120° C. at 2.67 kilopascals (20 mm Hg) pressure for three hours. Allow the resulting sample to cool and decant off product. The resulting product has the following structure and serves as the precursor for the pendant group $R^1$ in the present examples:

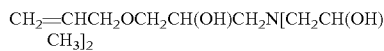

Synthesis of Elastomers

Prepare the following elastomers by first functionalizing a starting polysiloxane with the $R^1$ precursor prepared as described above and then crosslink the resulting functionalized polysiloxane with the crosslinker indicated for each example. Prepare the Comparative Examples in similar manner but without functionalizing the starting polysiloxane with $R^1$.

The starting polysiloxane is a dimethylmethylhydrogen siloxane having an average formula of $(CH_3)_3SiO[(CH_3)_2SiO]_{91}[(CH_3)HSiO]_{15}Si(CH_3)_3$, where there is 0.198 weight-percent H as Si—H.

Example 1 and Comparative Example A—Elastomer with 1,5-Hexadiene Crosslinker

Example 1

Into a 118 milliliter (4 ounce) squat jar containing a 2.54 centimeter star shaped magnetic stirrer, add 19.28 g of starting polysiloxane, 4.87 g of the $R^1$ precursor prepared as described above, and 93.0 g 2,2,4,6,6, pentamethylheptane. Place the jar with the contents into a 70° C. water bath above a magnetic stirrer controller. Heat the contents up to 70 degrees Celsius (° C.). Add 0.2 g 1,3-diethyl-1,1,3,3-tetramethyldisiloxane platinum complex (for example, SYL-OFF™ 4000 available from The Dow Chemical Company) and allow to react while stirring for 30 minutes. Then add 0.85 g of 1,5 hexadiene and 0.4 g 1,3-diethyl-1,1,3,3-tetramethyldisiloxane platinum complex (for example, SYL-OFF™ 4000 available from The Dow Chemical Company) and allow the material to gel. After gelation, place the sample in an oven at 70° C. for three hours to cure.

The resulting elastomer has a structure of Formula (I) wherein subscript a is approximately 95, subscript b is approximately 9, subscript c is approximately 6, $R^1$ has the structure of Formula (II) where n is 2, p is 1, q is 1 and wherein $R^2$ and $R^{2'}$ are both isopropyl (—$CH_2CH(OH)CH_3$), and X is —$CH_2(CH_2)_4CH_2$— that is bound to two siloxane backbone polymers in like manner as shown in Formula (I).

Comparative Example A. Prepare Comparative Example A in like manner as Example 1 except do not include any $R^1$ precursor component. The resulting elastomer is similar to Example 1 except the elastomer has a hydrogen on the silicone instead of $R^1$ the elastomer.

Example 2 and Comparative Example B—Elastomer with bis Allyl Poly(propylene oxide) Crosslinker Example 2

Into a 118 milliliter (4 ounce) squat jar containing a 2.54 centimeter star shaped magnetic stirrer, add 8.39 g of starting polysiloxane, 2.01 g of the $R^1$ precursor prepared as described above, and 60.0 g 2,2,4,6,6, pentamethylheptane. Place the jar with the contents into a 70° C. water bath above a magnetic stirrer controller. Heat the contents up to 70° C. Add 0.2 g 1,3-diethyl-1,1,3,3-tetramethyldisiloxane platinum complex (for example, SYL-OFF™ 4000 available from The Dow Chemical Company) and allow to react while stirring for 30 minutes. Then add 4.6 g of a material having an average structure of:

(Available as "DUS-80" from Nippon Oil and Fats) and 0.2 g 1,3-diethyl-1,1,3,3-tetramethyldisiloxane platinum complex (for example, SYL-OFF™ 4000 available from The Dow Chemical Company) and allow the material to gel. After gelation, place the sample in an oven at 70° C. for three hours to cure.

The resulting elastomer has a structure of Formula (I) wherein subscript a is approximately 95, subscript b is approximately 9, subscript c is approximately 6, $R^1$ has the structure of Formula (II) where n is 2, p is 1, q is 1 and $R^2$=$R^{2'}$=isopropyl (—$CH_2CH(OH)CH_3$), and X is:

—$CH_2CH_2CH_2[OCH(CH_3)CH_2]_{20}CH_2CH_2CH_2$— this bound to two siloxane backbone polymers each in like manner as shown in Formula (I).

Comparative Example B. Prepare Comparative Example B in like manner as Example 2 except do not include any $R^1$ precursor component. The resulting elastomer is similar to Example 2 except it contains hydrogen in place of $R^1$ on the elastomer.

Example 3 and Comparative Example C—Elastomer with Polysiloxane Crosslinker

Example 3

Into a 118 milliliter (4 ounce) squat jar containing a 2.54 centimeter star shaped magnetic stirrer, add 8.35 g of starting polysiloxane, 2.00 g of the $R^1$ precursor prepared as described above, and 60.0 g 2,2,4,6,6, pentamethylheptane. Place the jar with the contents into a 70° C. water bath above a magnetic stirrer controller. Heat the contents up to 70° C. Add 0.2 g 1,3-diethyl-1,1,3,3-tetramethyldisiloxane platinum complex (for example, SYL-OFF™ 4000 available from The Dow Chemical Company) and allow to react while stirring for 30 minutes. Then add 12.65 g of a 100 centistokes (cst) vinyl terminated polydimethylsiloxane (CAS #68083-19-2, available as DMS-V21 from Gelest) having an average structure of $CH_2$=$CH_2Si(CH_3)_2O[(CH_3)_2SiO]_{46}Si(CH_3)_2CH_2$=$CH_2$, and 0.2 g 1,3-diethyl-1,1,3,3-tetramethyldisiloxane platinum complex (for example, SYL-OFF™ 4000 available from The Dow Chemical Company) and allow the material to gel. After gelation, place the sample in an oven at 70° C. for three hours to cure.

The resulting elastomer has a structure of Formula (I) wherein subscript a is approximately 95, subscript b is approximately 9 and subscript c is approximately 6, $R^1$ has the structure of Formula (II) where n is 2, p is 1, q is 1, and $R^2$ and $R^{2'}$ are both isopropyl (—$CH_2CH(OH)CH_3$), and X is:

—$CH_2CH_2Si(CH_3)_2O$—$[Si(CH_3)_2O]_{46}SiCH_2CH_2$— that is bound to two siloxane backbone polymers each in like manner as shown in Formula (I).

Comparative Example C. Prepare Comparative Example C in like manner as Example 3 except do not include any $R^1$ precursor component. The resulting elastomer is similar to Example 3 except it has a hydrogen in place of $R^1$ in the elastomer.

Example 4

Elastomer with Poly(ethylene oxide) Crosslinker

Into a 118 milliliter (4 ounce) squat jar containing a 2.54 centimeter star shaped magnetic stirrer, add 9.80 g of starting polysiloxane, 2.35 g of the $R^1$ precursor prepared as described above, and 60.0 g 2,2,4,6,6, pentamethylheptane. Place the jar with the contents into a 70° C. water bath above a magnetic stirrer controller. Heat the contents up to 70° C. Add 0.2 g 1,3-diethyl-1,1,3,3-tetramethyldisiloxane platinum complex (for example, SYL-OFF™ 4000 available from The Dow Chemical Company) and allow to react while stirring for 30 minutes. Then add 2.85 g of a material having an average structure of:

$CH_2$=$C(CH_3)CH_2[OCH_2CH_2]_{13}CH_2C(CH_3)$=$CH_2$ (Available as DMUS-5 from Nippon Oil and Fats) and 0.2 g 1,3-diethyl-1,1,3,3-tetramethyldisiloxane platinum complex (for example, SYL-OFF™ 4000 available from The Dow Chemical Company) and allow the material to gel. After gelation, place the sample in an oven at 70° C. for three hours to cure.

The resulting elastomer has a structure of Formula (I) wherein subscript a is approximately 95, subscript b is approximately 9, subscript c is approximately 6, $R^1$ has the structure of Formula (II) where n is 2, p is 1, q is 1 and wherein $R^2a$ and $R^{2'}$ are both isopropyl (—$CH_2CH(OH)CH_3$), and X is:

—$CH_2CH(CH_3)CH_2[OCH_2CH_2]_{13}CH_2CH(CH_3)$
$CH_2$— that is bound to two siloxane backbone polymers each in like manner as shown in Formula (I).

Characterization of Elastomers

Characterize the elastomers of Examples (Exs) 1-4 and Comparative Examples (Comp Exs) A-C according to the Water Uptake Screening and Organic Solvent Compatibility methods described above. For the Solvent Compatibility characterization, evaluate using three different solvents: C12/15 alkyl benzoate, Capryllic/Capric Triglyceride and ethanol. Solvent Compatibility is only reported for the Examples.

Results for Water Uptake are in Table 1. Results for Solvent Compatibility are in Tables 2-4. Results indicate that desirable Water Uptake values are obtained when the $R^1$ group is present, but not when $R^1$ is absent for each of the different crosslinkers. Suitable solvent compatibility is also obtained with the inventive elastomers. Notably, desirable Water Uptake values and solvent compatibility is obtained for all Examples in an absence of pendant polyalkylene oxide groups and for Examples 1 and 3 in an absence of any polyalkylene oxide groups.

TABLE 1

| Example | Water Uptake (weight-percent) |
|---|---|
| Hexadiene Crosslinker | |
| Comp Ex A | 0 |
| Ex 1 | 74 |
| Bis Allyl poly(propylene oxide) Crosslinker | |
| Comp Ex B | <5 |
| Ex2 | 83 |
| Polysiloxane Crosslinker | |
| Comp Ex C | 0 |
| Ex 3 | 70 |
| Bis Allyl poly(ethylene oxide) Crosslinker | |
| Ex 4 | 88 |

TABLE 2

| | C12/15 alkyl benzoate | | |
|---|---|---|---|
| Example | Clarity Ranking | Viscosity Ranking | Homogeneous? |
| Ex 1 | Clear (10) | 10 | Homogeneous |
| Ex 2 | Clear (10) | 10 | Homogeneous |
| Ex 3 | Clear (10) | 10 | Homogeneous |
| Ex 4 | Clear (10) | 10 | Homogeneous |

TABLE 3

| | Capryllic/Capric Triglyceride | | |
|---|---|---|---|
| Example | Clarity Ranking | Viscosity Ranking | Homogeneous? |
| Ex 1 | Clear (10) | 10 | Homogeneous |
| Ex 2 | Clear (10) | 10 | Homogeneous |
| Ex 3 | Clear (10) | 10 | Homogeneous |
| Ex 4 | Clear (10) | 10 | Homogeneous |

TABLE 4

| | Ethanol | | |
|---|---|---|---|
| Example | Clarity Ranking | Viscosity Ranking | Homogeneous? |
| Ex 1 | Clear (10) | 10 | Homogeneous |
| Ex 2 | Slight Haze (8) | 10 | Homogeneous |
| Ex 3 | Slight Haze (8) | 10 | Homogeneous |
| Ex 4 | Slight Haze (8) | 10 | Homogeneous |

What is claimed is:

1. An elastomer comprising multiple siloxane backbone polymers interconnected by two or more than two crosslinker remnants where the elastomer has the general structure of Formula (I):

$$(CH_3)_3SiO-[Si(CH_3)_2)O]_a-[Si(CH_3)(R^1)O]_b-[Si(CH_3)O]_c-Si(CH_3)_3 \quad (I)$$
$$|$$
$$X$$

where:
subscript a is independently in each siloxane backbone polymer a number in a range of 50 to 500,
subscript b is independently in each siloxane backbone polymer a number in a range of one to 10,
subscript c is independently in each siloxane backbone polymer a number in a range of 2 to 30, and $R^1$ has the structure of Formula (II):

$$-CH_2(CH_2)_nO(CH_2)_pCH(OH)(CH_2)_qNR^2R^{2'}$$

where subscripts n, p and q are each independently in each occurrence a number in a arrange of one to 5 and $R^2$ and $R^2$ are independently in each occurrence selected from a group consisting of alkyl and hydroxyalkyl groups having one or more and at the same time 5 or fewer carbon atoms; and where X is a crosslinker remnant bound to a siloxane unit corresponding to subscript c of a siloxane backbone polymer in addition to the one shown in Formula (I) so that the crosslinker remnant in each occurrence is a reaction product with two siloxane backbone polymers, wherein the crosslinker is selected from a group consisting of primary organic dienes, divinyl siloxane and polyoxyalkylenes wherein at least two X components correspond to crosslinker remnants connecting the same two siloxane backbone polymers.

2. The elastomer of claim 1, wherein the elastomer is free of pendant polyalkylene oxide groups.

3. The elastomer of claim 1, wherein subscript c is independently in each siloxane backbone polymer a number in a range of 2 to 8.

4. The elastomer of claim 1, wherein $R^1$ has the structure of Formula (III):

$$-CH_2(CH_2)_2OCH(OH)CH_2N[CH_2CH(OH)(CH_3)]_2.$$

5. The elastomer of claim 1, wherein the elastomer is free of poly(alkylene oxide) groups.

6. The elastomer of claim 1, wherein the crosslinker remnant is any one or any combination of more than one component selected from a group consisting of alkylenes, linear polysiloxanes, and branched polysiloxanes.

7. A formulation comprising the elastomer of claim 1, in combination with an organic solvent.

8. The formulation of claim 7, wherein the formulation further comprises a continuous aqueous phase in combination with the elastomer and the organic solvent.

9. The formulation of claim 7, wherein the formulation further comprises any one or any combination of more than one personal care product additive selected from a group consisting of anionic surfactants, cationic polymers, fatty acid aklanolamides, amine oxides, acyl derivatives, polyols, oils, waxes, vitamins, colorants, and fragrant additives.

10. The formulation of claim 7, wherein the formulation is in the form of a personal care product.

* * * * *